(12) United States Patent
Lee

(10) Patent No.: US 7,785,848 B2
(45) Date of Patent: Aug. 31, 2010

(54) BIOMASS CONVERSION PERFORMANCE USING IGNEOUS PHYLLOSILICATE MINERALS WITH HIGH EMISSION OF FAR-INFRARED LIGHT

(75) Inventor: Hyo C. Lee, Addison, IL (US)

(73) Assignee: ACTIVA BioGreen, Inc., Bloomingdale, IL (US)

( * ) Notice: Subject to any disclaimer, the term of this patent is extended or adjusted under 35 U.S.C. 154(b) by 642 days.

(21) Appl. No.: 11/439,726

(22) Filed: May 23, 2006

(65) Prior Publication Data
US 2007/0275446 A1    Nov. 29, 2007

(51) Int. Cl.
C12P 7/06    (2006.01)
C12N 1/16    (2006.01)
(52) U.S. Cl. .................. 435/161; 435/255.2; 250/493.1; 250/495.1
(58) Field of Classification Search .................. 435/161, 435/255.2; 250/493.1, 495.1
See application file for complete search history.

(56) References Cited

U.S. PATENT DOCUMENTS

| | | | |
|---|---|---|---|
| 3,850,753 A * | 11/1974 | Chibata et al. .............. | 435/248 |
| 4,420,561 A * | 12/1983 | Chen et al. .................. | 435/161 |
| 4,886,972 A * | 12/1989 | Nakai et al. ............. | 250/504 R |
| 5,472,720 A | 12/1995 | Rakhimov et al. | |
| 5,542,194 A | 8/1996 | Hanzawa et al. | |
| 5,707,911 A | 1/1998 | Rakhimov et al. | |
| 6,051,202 A * | 4/2000 | You ........................ | 423/328.1 |
| 6,420,146 B1 | 7/2002 | Ramakrishna et al. | |
| 6,509,180 B1 | 1/2003 | Verser et al. | |
| 6,569,670 B2 | 5/2003 | Anderson et al. | |
| 6,927,048 B2 | 8/2005 | Verser et al. | |
| 2002/0137154 A1 | 9/2002 | Ingram et al. | |
| 2005/0026261 A1 * | 2/2005 | Otto et al. ................... | 435/161 |
| 2005/0136520 A1 | 6/2005 | Kinley et al. | |

FOREIGN PATENT DOCUMENTS

| | | | |
|---|---|---|---|
| JP | 01317163 A | * | 12/1989 |
| JP | 11057037 A | * | 3/1999 |
| KR | 0208878 B1 | | 8/1998 |
| KR | 2003083356 A | * | 10/2003 |

OTHER PUBLICATIONS

Industrial ethanol. 2005. http://web.archive.org/web/20050225234520/http://www.fermentis.com/FO/EN/08-Ethanol/30-10_directions_eth.asp.*
Ergun et al. 1997. Improved Ethanol Production by Saccharomyces cerevisiae with EDTA, Ferrocyanide and Zeolite X Addition to Sugar Beet Molasses. J. Chem. T ech. Biotechnol. 68, 147-150.*
Minerals Information on Mica from USGS. 2009; http://minerals.usgs.gov/minerals/pubs/commodity/mica/ p. 1-2.*
Dale et al., "Enzymatic Simultaneous Saccharification and Fermentation (SSF) of Biomass to Ethanol in a Pilot 130 Liter Multistage Continuous Reactor Separator," Bioenergy 2000: Moving Technology into the Marketplace, Final Report, retrieved from web page http://www.nrbp.orq/papers/049.pdf. (2000).
Dellweg, Biotechnology, Verlag Chemie, Weiheim, 3, pp. 257-260, 335-343 (1983).
Hatfield et al., "Improved Microscopic Yeast Cell Counting," Journal of the American Society of Brewing Chemists, 46, pp. 123-125 (1988).
Ingledew, "Understanding the Biochemistry of Alcohol Production," The Alcohol Textbook Edited by Lyons et al., $2^{nd}$ Ed., Nottingham University Press, Nottingham, United Kingdom, Chapter 7 (1995).
Kirsop, "Developments in Beer Fermentation," Topics in Enzyme and Fermentation Technology, 6, pp. 79-131 (1982).
Schwenk et al., "Water: The Element of Life," Translated by Marjorie Spock, Anthroposophic Press, Great Barrington, MA, pp. 159-176 (1982).
Walker et al., "Yeast Physiology and Biotechnology," John Wiley and Sons Ltd., United Kingdom, pp. 149-169 (1999).

* cited by examiner

Primary Examiner—Taeyoon Kim

(57)   ABSTRACT

The present invention relates to applications of far-infrared-inducing natural minerals to improve biomass conversion performance by promoting the growth of microbes, especially in the fermentation process. The present invention further relates to the enhancement of other enzyme reactions during the fermentation process. The present invention is applicable for use in corn-to-ethanol fermentation to increase the ethanol productivity as well as for yeast manufacturing.

18 Claims, 7 Drawing Sheets

BIOMASS CONVERSION PERFORMANCE USING IGNEOUS PHYLLOSILICATE MINERALS WITH HIGH EMISSION OF FAR-INFRARED LIGHT

FIELD OF THE INVENTION

The present invention relates to a method for improving the biomass conversion process. More specifically the invention relates to an application of far-infrared-inducing natural minerals to the microbial fermentation, in particular for the ethanol production with a dry or wet milling process. The invention further relates to the enhancement of enzyme reactions, in particular for the production of fermentable sugars. The invention also relates to yeast manufacturing.

BACKGROUND OF THE INVENTION

Bioconversion processes of carbohydrates to their cellular compounds have become increasingly important, providing a variety of advantages over non-biological conversion processes. Due to the abundant availability of natural resources for bioconversion processes, various technologies have been applied to the production of chemicals and fuels, food fermentation and waste water treatment. Over the past 25 years, there has been rapid progression in the production of liquid biofuels in context with alternative routes of bioconversion of biomass. There has been a great deal of development by researchers in those routes depending on the activity of plant cell wall degrading enzymes, as well as the conventional routes to bioethanol from corn, sugar beet, wheat or other cereal grains.

Soaring demand and limited supply of gasoline has resulted in recent drastic price hikes and this trend is expected to continue. Price and environmental concerns are resulting in increased awareness and demand for alternative fuel sources. The United States currently produces over 4.6 billion gallons of fuel ethanol at 102 plants using 1.7 billion bushels of corn each year and plans to increase rapidly in annual production capacity en route to 7.5 billion gallons in the next few years. Considering the current annual domestic gasoline consumption of 140 billion gallons, the biofuel of ethanol is only 3.2% of domestic fuel production necessary for automobiles. However, the fuel ethanol would be a short-term option to diversify fuel sources, not to mention its positive impact on the environmental and the greenhouse effects. For renewable fuels, the U.S. Department of Agriculture reported that every 1 Btu of petroleum fuel used to produce ethanol generates 13.2 Btu's, thereby greatly enhances domestic energy security.

Currently, ethanol is produced mainly from corn starch using the yeast of *Saccharomyces Cerevisiae* strains. To meet the future renewable fuels standard (RFS) requirement in the U.S., however, relatively inexpensive raw materials of celluloses such as hemicelluloses and lignocelluloses are seriously being pursued to further reduce production costs of the fuel ethanol. The Renewable Fuels Association (RFA) is targeting for 250 million gallons of the annual cellulosic ethanol production by 2012.

During the production of ethanol, ethanologenic microorganisms, such as mesophilic ethanologenic microorganisms, are able to grow and efficiently ferment sugars at pH's between 3.8-6.0 and temperatures from 82 to 95° F. Under ideal incubation conditions, microorganisms grow with basic nutrients, mainly comprised of water, carbon and nitrogen sources, phosphorus, and vitamins and minerals.

However, the growth of microbial cells is inhibited by many stress factors under industrial fermentation conditions, including physical stresses of temperature, osmotic pressure and plasmolysis, chemical stresses of alcohol inhibition, oxidation, acidity, toxicity and mutagenesis, and biological stresses of cellular aging, genetypic changes and competition from other microorganisms (Walker, G., Yeast Physiology and Biotechnology, John Wiley and Sons Ltd., United Kingdom, (1999)). Accordingly, it is necessary to find a way to promote the growth of microorganisms in order to achieve the maximal fermentation productivity.

Several technologies have currently been introduced to improve the fermentation process, especially for the production of fuel ethanol. Such a technology is disclosed in pending U.S. Patent Application Publication No. US 2002/0137154, for the use of acetaldehyde and other glycolic metabolites as nutrient additives. However, it may not be a practical alternative for an industrial fermentation process due to environmental and economic issues related to nutrients.

Other technologies, including the use of ultrasonic energy (U.S. Patent Application Publication No. US 2005/0136520), and addition of dicarboxylic acids (U.S. Pat. No. 6,569,670) for the improvement of bioconversion processes are more related to enzymatic hydrolysis reactions altering rheologies of fluid media. In addition, these technologies are not related to the improvement of the growth of microorganisms that is critical for the fermentation, especially under the industrial stressful environment.

Using infrared radiation, several technologies are disclosed to apply directly for industrial heating devices. U.S. Pat. Nos. 5,472,720 and 5,707,911 disclose the treatment of ceramic materials with infrared radiation, and the manufacturing of ceramic materials for infrared dryer and stabilizer, respectively. U.S. Pat. No. 5,542,194 also discloses far-infrared radiating ceramic materials mainly of SiC for heating apparatus, claiming excellent anticorrosivity and radiation capabilities. However, all these ceramic materials for industrial heating devices are not suitable for biological conversion processes due to their chemical and physical characteristics.

Therefore, there is a continued need for more effective technologies for improving the fermentation processes and subsequent improvement of bioconversion productivities, thus producing economic and environmental benefits. Accordingly, the object of the invention is to provide a method for improvement of the growth of microorganisms required for bioconversion processes and for reducing the cost of bioconversion products.

SUMMARY OF THE INVENTION

The objective of the present invention is directed to a method of promoting the growth of microorganisms (microbes) and improving the microbial fermentation performance via the employment of multi-dimensional phyllosilicate natural minerals with a capability for emitting far-infrared (FIR) electro-magnetic rays with a range of wavelength of about 5 to 20 µm. These minerals are FIR-inducing natural minerals. This frequency range is known to be matched with the natural resonant frequency range of water molecules. These FIR-inducing natural minerals can provide emittances higher than about 0.90, preferably 0.93, based on an ideal blackbody at 60-120° F.

FIR-inducing natural minerals include, but are not limited to, agalmatolite, albite, anorthite, antigorite, aplite, betalite, biotite, char coal, chlorite, clinochlore, clinoptillolite, felstone, garnet, glauconite, granite, illite, jade, kaolinite, kyanite, leonardite, mica, microcline, monazite, montmorillonite, muscovite, olivine, orthoclase, pascalite, pegmatite, phlogopite, plagioclase, pyrophyllite, sanidine, sericite, sepiolite, serpentine, sillimanite, staurolite, tourmaline, volcano ash, other zeolites, and combinations thereof.

In the embodiments of the present invention, the FIR-inducing natural minerals are used in the form of a fine powder of at least about 100 mesh, or higher (that is, finer mesh). Preferably, the FIR-inducing natural minerals are used in the form of an ultra-fine powder of about 400 mesh, or higher.

Any objects with sufficient water can be effectively activated via radiation of far-infrared light, which increases the resonance frequency rate of water. While electro-magnetic rays with short wavelength such as gamma, ultra-violet, etc. are considered harmful, far-infrared light with relatively long wavelength is a safe energy ray and very effective for stimulating the growth of living objects with water.

These principles can be applied to the growth of microorganisms that need water for growth and metabolism, including yeast cells. These same mechanisms are applied to stimulate the fermentation metabolism of yeasts for alcohol production as well as yeast manufacturing. The potential energy of water is modulated to higher levels favorable for the growth of yeast cells in the presence of such FIR-inducing minerals. Thus the overall fermentation performance is improved, along with enhancement of related enzyme reactions.

It is, therefore, an object of the present invention to provide a favorable environment for the yeast growth that is closely linked to a bioconversion performance. In a particular application, the present invention is applied for promoting the microbial growth factor by about 10-30% and subsequently improving the ethanol productivity (i.e., production) by about 0.3-0.5% ethanol weight/mash volume (wt/vol) higher than the current state of the art by implementing a small but effective amount of FIR-inducing minerals with finely-divided particles as illustrated in the embodiment of plant trials.

In another embodiment of the present invention, there is provided a fermentation system including a propagation tank for initial exponential growth of microbes, containing FIR-inducing natural minerals, and a fermenter for continued growth of microbes, optionally containing FIR-inducing natural minerals.

One advantage of the present invention is related to economic benefits, since the concentration of the new minerals is about part per million (ppm) levels in a fermentation reactor. Based on the current conversion factor for the corn-to-fuel ethanol production, such improvements are corresponding to an additional ethanol production of 0.06-0.10 gal/bushel. This improvement translates to the savings of approximately one half million dollars per year for a typical ethanol plant with an annual ethanol production capacity of 40 million gallons. Similar cost reductions are expected for yeast manufacturing, boosting yeast productivities by employing the present invention for the culture propagation and fermentation processes.

Another advantage of the present invention is a value-added co-product of distiller's dried grains and solubles (DDGS), which are blended with FIR-inducing minerals after the separation from fermented products during the ethanol production, even though it is a low concentration. Natural minerals are often applied to livestock feed additives for benefits in digestibility, fortification of natural balance with trace minerals, binding with toxins and other health-related areas.

DETAILED DESCRIPTION OF THE INVENTION

Figure 1:
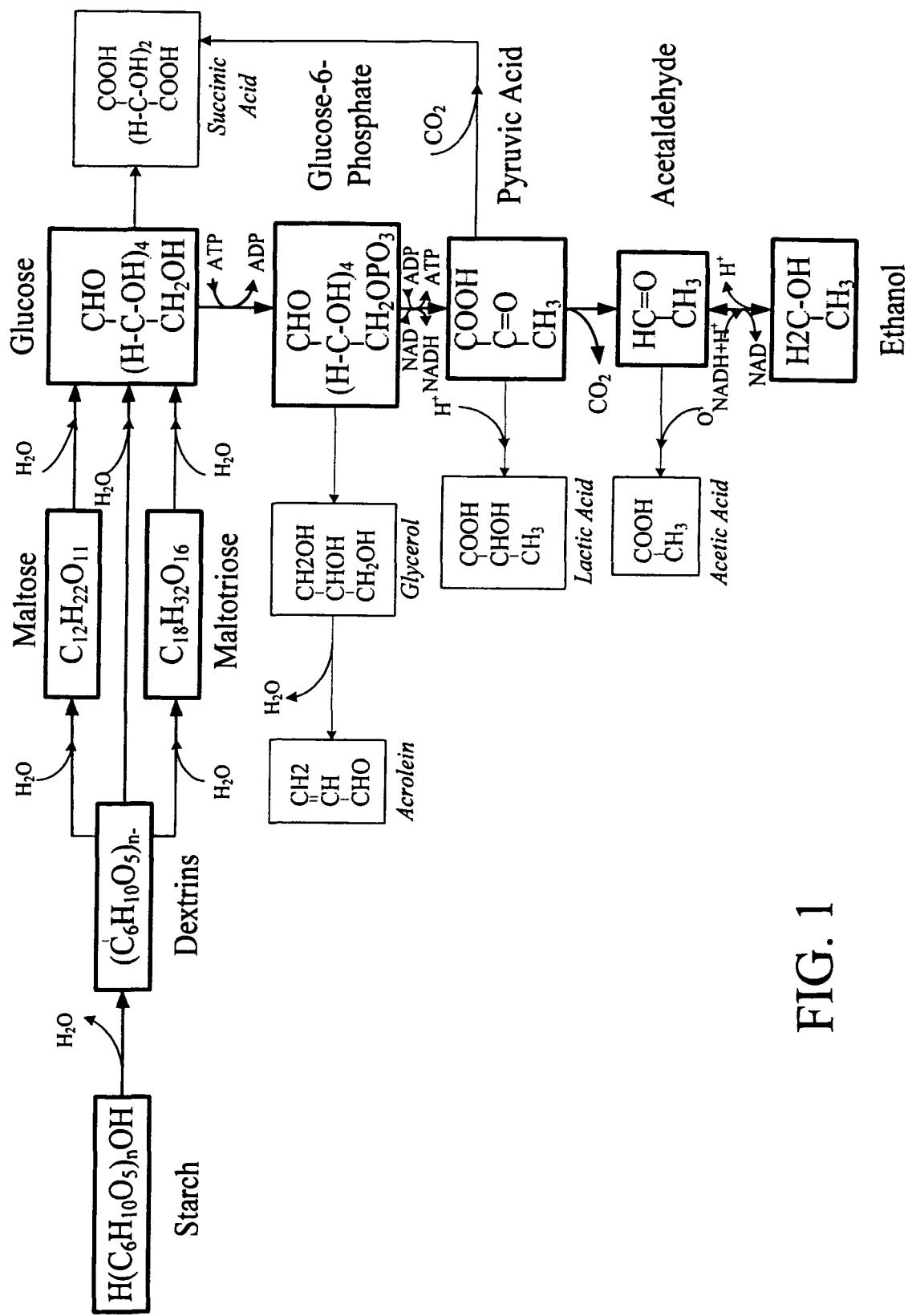
FIG. 1 shows the general pathways for the corn-to-ethanol reaction mechanisms via an Embden-Meyerhof-Pamas (EMP) glycolysis and other microbial pathways referred to in example embodiments of the present invention.

In its principal embodiment, the present invention is directed to a method for increasing the growth of microbes by applying FIR-inducing natural minerals to a biomass conversion process. FIR-inducing minerals include alumino-silicate salts that emit far-infrared radiation with a range of wavelength of about 5 to 20 µm. The preparation of FIR-inducing crystalline materials is described in Korean Patent No. 208,878, hereby incorporated by reference.

Useful FIR-inducing natural minerals include, but are not limited to, agalmatolite, albite, anorthite, antigorite, aplite, betalite, biotite, char coal, chlorite, clinochlore, clinoptillolite, felstone, garnet, glauconite, granite, illite, jade, kaolinite, kyanite, leonardite, mica, microcline, monazite, montmorillonite, muscovite, olivine, orthoclase, pascalite, pegmatite, phlogopite, plagioclase, pyrophyllite, sanidine, sericite, sepiolite, serpentine, sillimanite, staurolite, tourmaline, volcano ash, other zeolites, and combinations thereof.

The first stage of the process according to the present invention is the preparation of the natural mineral slurry. The process consists of a step of diluting the FIR-inducing minerals with clean warm water to about 5-40% and preferably to about 15-25% of the weight of the mineral.

For the next step, the slurry of FIR-inducing mineral is introduced during the hydration of yeasts under good agitation, in order to disperse well in the yeast hydration solution for effective contacts between the minerals and yeast cells. A desirable dosage ratio of the FIR-inducing natural mineral powder depends on incubation conditions, and can be used in an amount of about 0.5-25% by weight based on the total initial weight of the microbes (yeasts), but preferably about 1-5% of the total yeasts by weight. A dispersant is often applied to improve suspension of minerals during blending. Useful dispersants include a hydrophilic biopolymer like polysaccharides, which are recommended for colloidal suspension. After mixing with the hydrated yeasts, the slurry is transferred to a yeast conditioning process. Other lipid-based yeast foods are also introduced to a yeast conditioning tank, even though the majority of nutrients for the yeast growth are driven from fermentation mash as well as thin stillage.

For a continuous process, the FIR-inducing minerals are introduced upstream of a prefermenter. Preferably the mineral powder is mixed with warm water to about 15-25% of the weight of the mineral powder and metered to a conversion tanks or introduced further upstream to a slurry tank or other process units with a mixing device.

The characteristics of the yeast conditioning process are greatly influenced by yeast incubation conditions. Oxygen in the form of compressed air is supplied steadily during conditioning to promote the growth of yeasts under a respiratory environment. Typical propagation conditions for an industrial batch fermentation process for the ethanol production are:

| | |
|---|---|
| Temperature: | 92-94° F. |
| pH: | 4.8-5.4 |
| Solid content: | 12-14 Brix |
| Free amino nitrogen (FAN): | >200 mg/l |

The propagation of yeast cells is completed when the exponential growth pattern levels off, such as:

$$\tau = \ln(x/x_o)/\mu_{max} \quad (1)$$

where, $\tau$=propagation time, x=yeast CFU, $x_o$=the initial yeast CFU, and $\mu_{max}$=exponential growth factor.

The exponential growth factor is expected to increase in the presence of FIR-inducing minerals, resulting in accelerated yeast growth. The maximal anaerobic specific growth rate of yeast is reported to be $\mu_{max}$=0.35/hr at the state of the art industrial ethanol plant (Dellweg, H., Biotechnology, Verlag Chemie, Weinheim, 3,257-385, (1983)).

For a typical target of the yeast cell densities around 250-350 millions/ml, propagation conditions of temperature, pH, free amino nitrogen (FAN), aeration, etc. are critical to ensure an optimal growth of yeast cells for an in-direct pitching process. After discharging the inoculated yeasts to a fermenter, they grow for the second phase of the exponential growth. The FIR-inducing minerals play an important role for stimulating the continuous growth of next generation yeasts. Especially, the growth of *Saccharomyces Cerevisiae* for the ethanol bioconversion is coupled closely to the ethanol productivity. Accordingly, propagators and fermenters for further promoting the growth of microbes are designed to be coated on their inside (microbe-contacting) surfaces with FIR-inducing materials (including minerals) and/or equipped with devices that emit FIR rays including, but not limited to, ceramic plates and bars made of FIR-inducing materials.

A growing yeast cell produces ethanol, $CO_2$ and Adenosine Tri-Phosphate (ATP) at a rate 33-fold higher than stationary cells (Kirsop, B. H., Topics in Enzyme and Fermentation Technology, 6:7-131, 1982), as described in FIG. 1 for the corn-to-ethanol chemistries. Accordingly, it is becoming more critical to sustain a continuous growth of yeasts during a fermentation cycle, when yeast stress factors increase with an increase in ethanol production. High intracellular ethanol concentrations are the major inhibiting factor to the growth of yeasts during the fermentation process.

Water in living cells has a unique structure, and clusters of its molecules play an important role for biological reactions. As German engineer Theodor Schwenk and his Institute for Flow Science demonstrated for a concept of "living water" by photographing the internal structure water (Schwenk, T. and W. Schwenk, "Water: The Element of Life," Translated by M. Spock, Anthroposophic Press, (1989, Great Barrinton, Mass.), water can be activated by far-infrared energies. The hydrogen and oxygen bonds of water molecules have their own frequencies for vibration, bending and having a motion of torsion between O—H atoms.

A typical resonant frequency of water is about 6.27 μm, and most organic materials of living cells, including fermentation microbes, have resonant energies with the wavelength of 6-12 μm that is defined as a part of far-infrared ranges. Accordingly, electro-magnetic energies with the same frequencies can be applied to activate the systems of such living cells, for example. Several natural minerals have a capability for emitting far-infrared rays with the wavelength of 5-20 μm and for resonating the motions of water and organic materials. While resonating among molecules, typical biological energies are boosted by several-fold, enhancing the growth of microbes and metabolisms.

Furthermore, microbial cells absorb nutrients through the cell membrane as compounds dissolved in water. Accordingly, the transport of water is critical for the growth of microbes, since water permeability is often rate-limited for the overall bioconversion process by passage through both the yeast cell wall and plasma membrane. When water molecules are declusterized by resonant energies with high intensity of FIR-inducing minerals, influx and efflux of water across microbial plasma membrane are drastically enhanced for biosysnthesis and metabolism by microbial cells.

Fermentation sometimes undergoes stagnation, especially near the end of a fermentation cycle, when the concentration of ethanol approaches a maximum value for the process. In addition to high ethanol levels, poor aeration for $CO_2$ evolution, the role of temperature, high sulfur levels, etc. are also cited for stuck fermentation at industrial ethanol plants (Ingledew, W. M., "Understanding the Biochemistry of Alcohol Production," The Alcohol Textbook Edited by Lyons, T. P., Kelsall, D. R., and J. E. Murtagh, $2^{nd}$ Ed., Nottingham University press, Nottingham, UK, Chapter 7, (1995)). It was often observed the stuck fermentation is caused by the depletion of dissolved oxygen at the end of a fermentation cycle that is essential for the synthesis of sterol and unsaturated fatty acids necessary for the growth of yeast. It is obvious that such causes for stuck fermentation should be alleviated to provide satisfactory fermentation performance with a maximal alcohol productivity.

Bioconversion processes can include, for example, a biomass to ethanol process. Another bioconversion process is biomass to beneficial microbe, such as yeast (i.e., biomass to yeast). Beneficial yeasts can include, but are not limited to, compressed bakery yeast, active dry yeast, creamy yeast, feed yeast, and other yeast cultures.

During the production of ethanol, ethanologenic microorganisms, such as mesophilic ethanologenic microorganisms, are able to grow and efficiently ferment sugars. Useful ethanologenic microbes include thermo-tolerant yeast, such as yeast derived from *Saccharomyces* spp. Preferably, a strain of *Saccharomyces Cerevisiae* will be used.

The biomass for the bioconversion processes can include, but is not limited to, corn, barley, sorghum (milo), wheat, rye, rice, other cereal grains, cellulose, hemicellulose, lignocellulose, pectin, potatoes, and combinations thereof. The biomass, or the biomass media for the bioconversion processes can further include the sources of fermentable carbon, inorganic nitrogen, phosphate and dissolved oxygen.

Figure 2:
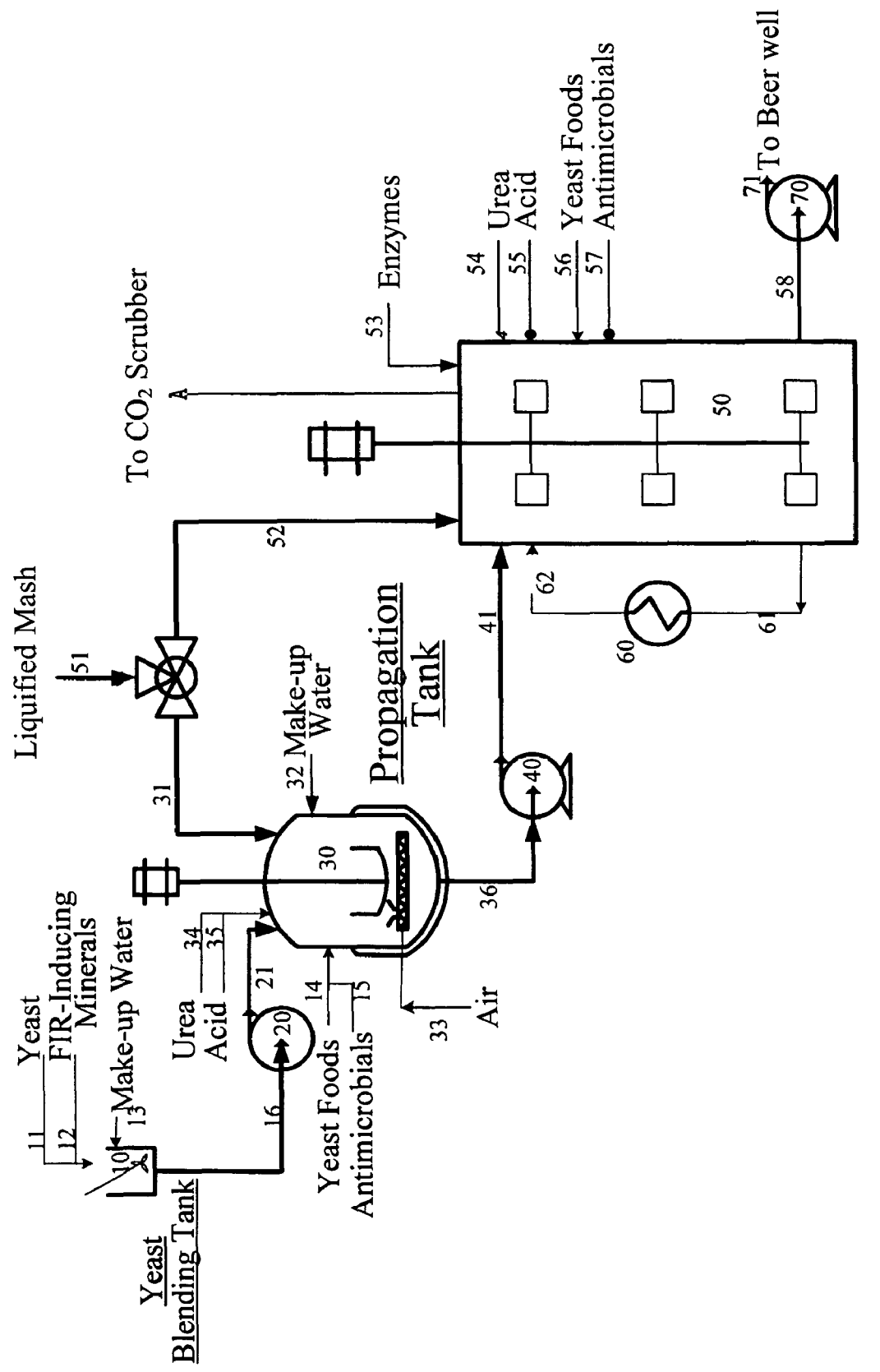
FIG. 2 is a schematic representation of the embodiment of that portion of the batch fermentation process of the present invention in which the far-infrared-inducing minerals are introduced to Yeast Blending Tank for promoting the yeast growth.

In the following description of a batch fermentation process for the ethanol production with the simultaneous saccharification and fermentation (SSF) process, reference is made to the schematic diagram with such a method for the implementation of FIR-inducing minerals, as illustrated in FIG. 2.

The yeast 11 is re-hydrated with make-up water 13 from plant operations in Yeast Blending Tank 10. During the re-hydration of yeast, a specific amount of FIR-inducing minerals 12, typically 1-5% of fermentation genera, is introduced to Yeast Blending Tank 10, after mixing with make-up water to make a slurry with 15-25% solids. The re-hydration of yeast continues in Yeast Blending Tank 10 at 100° F. for 30 minutes.

After the re-hydration, the yeast slurry is discharged to Propagation Tank 30 with good agitation, about one hour after starting to fill the tank with low level of mash with approx. 50:50 mix of liquefied mash 31 from a Jet Cooker and make-up water 32. Further, Propagation Tank 30 may be designed to be coated on the inside surface with FIR-inducing materials and/or equipped with devices that emit FIR rays such as ceramic plates or bars, in order to maximize the impact of FIR rays on microbes conditioning. Other yeast foods 14 and antimicrobials 15 are also introduced during filling Propagation Tank 30. Nitrogen sources of urea 34 or aqueous ammonium hydroxide are also metered to Propagation Tank 30 for a free amino nitrogen (FAN) around 200 ppm. Acid 35 is used to adjust the pH in the tank to a range of 4.8-5.6. The yeast propagation continues until an exponential growth of yeast cells is completed, typically for about 6-8 hours at 92-96° F. Propagation Tank 30 is equipped with an aeration system 33 for a respiratory yeast growth. Typical yeast cell counts are approximately 400 millions/ml after the yeast conditioning process.

After the propagation is completed after the end of an exponential growth of yeasts, the conditioned yeast slurry mixture is discharged to Fermenter 50. When the level of Fermenter 50 is about 10% filled, introduction of the glucoamylase enzyme 53 into Fermenter 50 is started. A specific feeding schedule is devised so as not to overproduce fermentable sugars during a fermentation cycle. Ideally, the saccharification is to be controlled just enough for covering a maximum allowable fermentation rate at a given fermentation time. Nitrogen sources of urea 54 or aqueous ammonium hydroxide are also metered to Fermenter 50 to give a free amino nitrogen (FAN) level around 150 ppm+, enough for a continuous growth of yeast. Acid 55 is used to adjust the initial pH in the tank to a range of 4.2-5.0. Other yeast foods 56 and antimicrobials 57 are also fed to Fermenter 50 while filling. A typical fermentation batch continues at 89-94° F. for about 45-55 hours until a depletion of fermentable sugars or until a desirable fermentation level is achieved. A cooling media 60 circulates inside or outside Fermenter 50.

Figure 3:
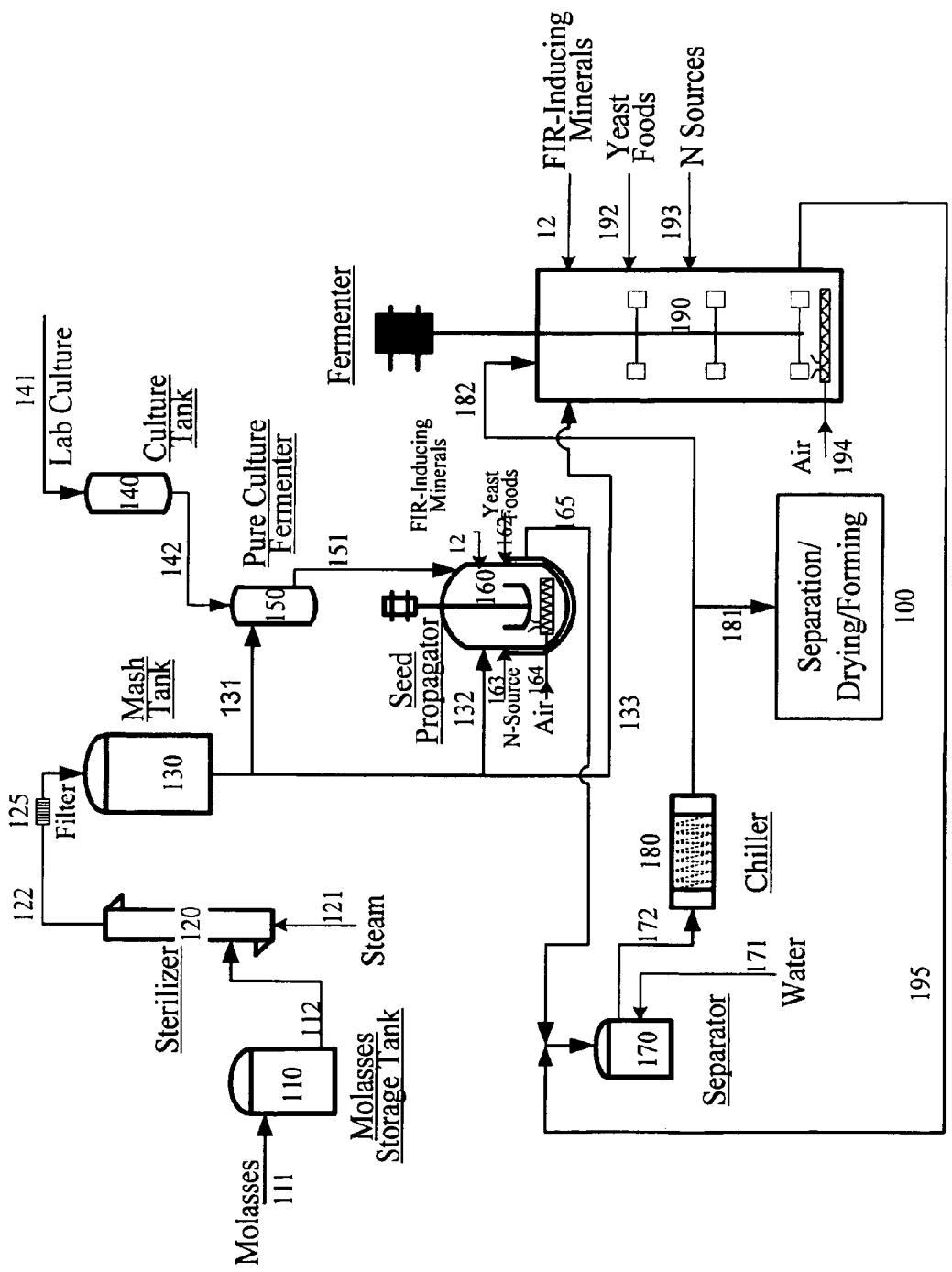
FIG. 3 is a schematic representation of the embodiment of that portion of the yeast manufacturing for the present invention in which the far-infrared-inducing minerals are introduced to Seed Propagator and Fermenter for promoting the yeast growth.

In addition to the ethanol production described above, the present invention can be applied to the manufacturing of compressed yeast, active dry yeast and yeast cultures by employing FIR-inducing minerals for the propagation and fermentation processes as illustrated in FIG. 3.

Molasses 111 from either sugar beets or sugar cane or a mixture of the two varieties is stored in Molasses Storage Tank 110 for a main carbohydrate source for the yeast manufacturing. First, the molasses is diluted with water to a proper concentration and adjusted for acidity with acid, prior to flash sterilizing in sterilizer 120 with steam 121. Secondly, molasses 111 is clarified and sterilized using steam to keep bacteria and other organisms from contaminating the yeast manufacturing.

A pure culture 141 that is known to contain vital genuine strain cells with desired characteristics is prepared for cultivation. This seed yeast culture, under careful control to maintain extreme purity, is allowed to grow in a laboratory and then transferred in a series of steps from laboratory flasks to larger containers. The stock culture is separated from the alcohol produced by the fermentation and stored in Culture Tank 140 under refrigeration. The stock culture is passed through Pure Culture Fermenter 150 for growing a pure culture that contains vital cells with desired characteristics and then fed to Seed Propagator 160 where the acidity is frequently adjusted through the addition of ammonium salts (N-source) 163. FIR-inducing minerals 12 of the present invention are introduced to Seed Propagator 160 for the maximum growth of yeast, along with other yeast foods 162 including biotin and phosphorus salts. Seed Propagator 160 is equipped with an aeration system 164 and controlled at a proper temperature for the growth of yeast cells. The propagation of stock yeast is continued in the presence of FIR-inducing minerals 12 until an exponential growth is completed. Yeast foods 162 are also introduced to Seed Propagator 160 to supply nutrients necessary for the growth of yeast.

Moreover, all fermenters 50 & 190, and propagator 160 may be designed to be coated inside the surface with FIR-inducing materials and/or equipped with devices that emit FIR rays such as ceramic plates and bars, in order to maximize the impact of FIR rays on microbial conditioning.

After propagation, the yeast mixture is passed through centrifugal pumps of Separator 170 where the mixture is washed and filtered, and then the cream yeast is fed to Fermenter 190 for further processing after passing through Chiller 180. The stock culture 133 is fed incrementally metered to Fermenter 190 to avoid the formation of alcohol during fermentation. FIR-inducing minerals 12 of the present invention are also introduced to Fermenter 190 for the maximum growth of yeast.

In general, the fermentation is continued with a series of fermenters, controlling the addition of nutrients 192 and aeration 194. The main consideration in the final stage of fermentation is an optimal balance of yeast characters in addition to a high yeast productivity. A proper drying system 100 is selected for a given type of yeast product. Several types of drying including belt, drum, spray and fluidized bed dryers are used for the manufacturing of active dry yeast.

The present invention is further described by referencing the following non-limiting examples that illustrate how the growth of microbes is influenced by the addition of FIR-inducing minerals for the improvement of fermentation productivities.

EXAMPLES

FIR-Inducing Materials (Fir-Inducing Natural Minerals)

Figure 4:
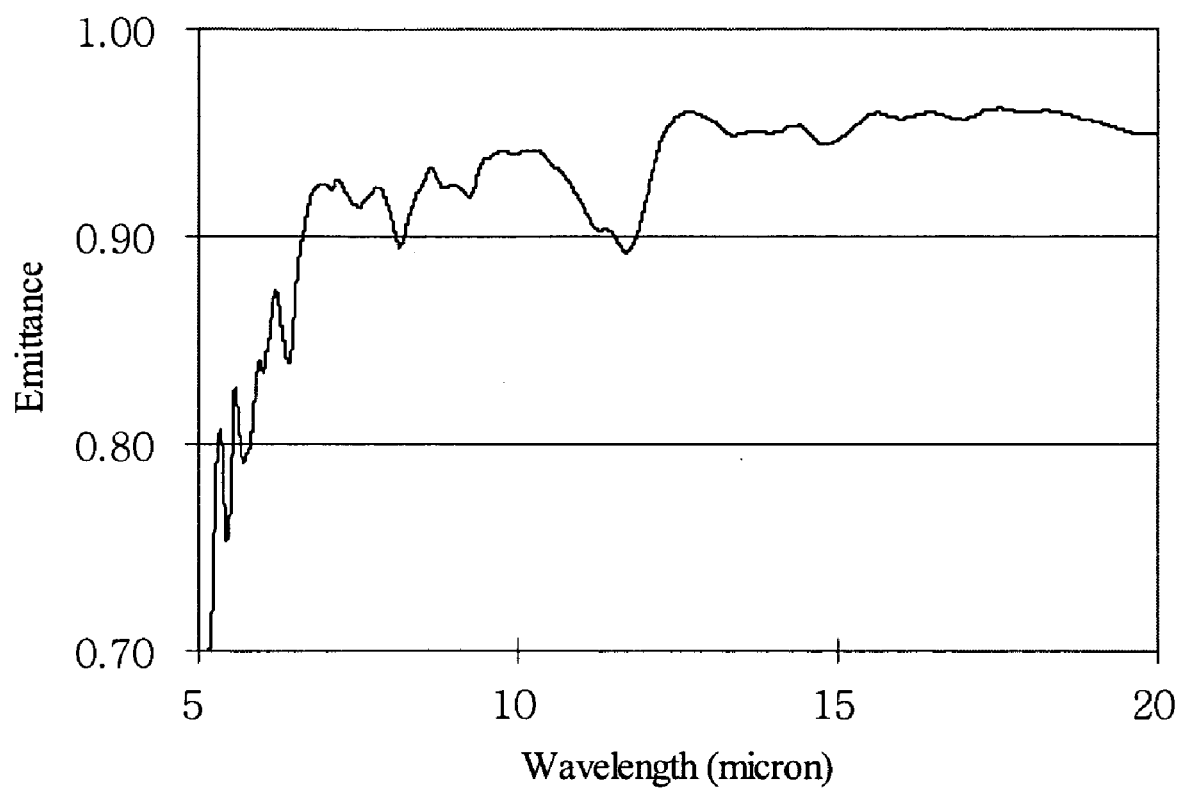
FIG. 4 is the spectral emittance data of the far-infrared-inducing mineral sample as a function of wavelength measured via a directional reflectometer.

The FIR-inducing mineral powder with a mesh size of about 1,200 (from ACTIVA BioGreen, Inc., Wood Dale, Ill.: Product No. 2205) manufactured via the method disclosed in Korean Patent No. 208,878 was used for testing at several ethanol plants. The total FIR spectral emittance was measured via Directional Reflectometer with Michelson-type Interferometer (Surface Optics Corp., Model 400T, San Diego, Calif.) as exhibited in FIG. 4, showing an average reflectance of 0.93 for the range of the wavelength of 5-20 µm.

Example 1

A plant trial was conducted at an ethanol production plant for 8 days using igneous phyllosilicate FIR-inducing natural minerals. This modern plant uses a dry milling corn process incorporating the Simultaneous Saccharification and Fermentation (SSF) technology. The plant has a capacity of 24 million gallons of the fuel ethanol production per year using No. 2 yellow corn. This plant trial differs from the other examples described here mainly in terms of relatively less use of backset for the slurry and cook tanks.

The initial step for the batch ethanol fermentation was the yeast inoculation, covering the hydration of the yeast. 150 lbs of the active dry yeasts of *Saccharomyces Cerevisiae* strains (Thermosacc® from Ethanol Technology, Milwaukee, Wis.)

was mixed with make-up water from plant operations to about 5% solid slurry. The slurry mixing was carried out in 150 gal Yeast Blending Tank at 100° F. for 20-30 minutes with good agitation. At an early stage of yeast hydration, 1 lb of igneous phyllosilicate FIR-inducing natural minerals ultra-fine powder (about 1,200 mesh ACTIVA Bio-Mineral™ (II) from ACTIVA BioGreen, Inc., Wood Dale, Ill.) was added to Yeast Blending Tank after making a 20-25% solid slurry with make-up water.

The next step is the conditioning/propagating of the yeast under operating conditions favorable for rapid growth of the yeast. The jet-cooked and liquefied mash with 30-31% dry solid was pumped slowly to a 30,000 gal Propagation Tank at a rate of 170 gpm, along with make-up water at 170 gpm. Approximately one hour after starting to fill the Propagation Tank, the hydrated yeast slurry mixture was introduced to the Propagation Tank, along with 2 gal of a starch hydrolysis enzyme of glucoamylase (Sprizyme® fuel from Novozymes North America. Inc., Franklinton, N.C.). Further, one gallon of yeast foods (AYF1177™ from Ethanol Technology, Milwaukee, Wis.) and 2 lb of antimicrobials (Lactoside™ from Ethanol Technology, Milwaukee, Wis.) were also added to the Propagation Tank after the completion of discharging the yeast slurry. In addition, 325 lbs of the urea solution (40% urea from Hydrite Chemical Co., Waterloo, Iowa) was added to the Propagation Tank to provide the free-amino-nitrogen required for the yeast biosynthesis. The yeast incubation was continued to achieve a stable maximum yeast growth for 7-8 hours under good agitation until the tank was completely filled with low mash slurry of 12 Brix at 92-96° F. During the propagation process, compressed air was introduced through a sparger at the bottom of the tank in order to promote the growth of yeasts. Sulfuric acid (93% min. from Hydrite Chemical Co., Waterloo, Iowa) was used to adjust the pH around to 5.0-5.3 during the yeast conditioning process.

The next main step is the simultaneous saccharification and fermentation process to produce ethanol from fermentable sugars via an Embden-Meyerhof-Parnas (EMP) glycolysis pathway. The cooked and liquefied mash with 24 Brix including about 15% backset was pumped at 525 gpm to a 360,000 gal fermenter. When the fermenter was about 10% filled with the mash, discharge of the inoculated yeast slurry to the fermenter was started, for one and a half hours. At the beginning of filling the fermenter, the urea solution with 1,200 lbs urea solution (40% urea from Hydrite Chemical Co., Waterloo, Iowa) was introduced to the fermenter and sulfuric acid was used to adjust the pH of the initial fermenting slurry to around 4.3-4.5. During filling of the fermenter, 25 gal of the aqueous hydrogen peroxide solution (35% $H_2O_2$ from Hydrite Chemical Co., Waterloo, Iowa) was being metered to the fermenter for promoting the growth of yeasts and controlling bacteria during filling of the fermenter. At the end of fermenter filling, 5 lbs of the yeast foods (AYF1177 from Ethanol Technology) was added to the fermenter. The fermenter off-gas line was open to the $CO_2$ header 12 hours after the fermenter started filling and closed after 18 hours continuous opening. The temperature of the fermenter was set at 88° F. under good agitation while the fermenter was being filled. The temperature was then raised to 93° F. upon completion of filling the fermenter. The fermenter temperature was held steady for the rest of the fermentation cycle.

During a fermentation cycle, an enzyme of glucoamylase (Sprizyme® fuel from Novozymes North America. Inc., Franklinton, N.C.) was employed for the hydrolysis of starch by metering it at a rate of 605 ml/min for the initial 7-8 hours. During the saccharification/fermentation cycle, the total amount of glucoamylase fed to the fermenter was 72 gal that are equivalent to 0.34 amyloglucosidase units (AGU) per gram of dry solid.

A typical schematic for a batch process of ethanol fermentation with the simultaneous saccharification and fermentation process is exhibited in FIG. 2.

During the saccharification/fermentation cycle, several mash samples were collected from the fermenter for the yeast cell count and HPLC analysis.

Using a color indicator of methylene blue and Hemacytometer's chambers, each fermentation sample was examined via a microscope at a 40 magnification (Nikon Model No. TE 2000 with a Motic digital camera) for the determination of CFU counts, viability index and budding index. Typically, 25 square grids covering a sample volume of 0.1 $mm^3$ were examined each time using a dilution technique (Journal of the American Society of Brewing Chemists, 46, 123 (1988). The final yeast counts were an average of multiple samples.

The plant trial was continued to process 24 fermentation batches and the average yeast cell count data was measured to be 200-240 millions/ml.

Using HPLC (Waters Breeze Model 2410 with Refractive Index Detector from Waters Corp., Milford, Miss.), each fermentation sample was analyzed for a fermentation product distribution. A typical turn-around time is 28 minutes for a complete analysis. The average ethanol productivity based on dextrose equivalent during the trial was derived to be 244.47 g/l with a standard deviation of 8.43.

The average fermentation performance of the plant trial is summarized in Table 1.

TABLE 1

Fermentation Performance of Plant Trial

| Fermentation Time | Yeast Cell Count (million/ml) | Average Ethanol Product @ dextrose equivalent (g/l) |
|---|---|---|
| 48 hr | 200-240 | 244.47 ± 8.43 |

Example 2

A second plant trial was conducted at an ethanol production plant for 11 days using igneous phyllosilicate FIR-inducing natural minerals. This modern plant uses a dry milling corn process incorporating the Simultaneous Saccharification and Fermentation (SSF) technology. This plant has a capacity of 50 million gallons of the fuel ethanol production per year using No. 2 yellow corn. This plant trial differs from the other examples described here mainly in terms of no employment of any kind of conventional yeast foods.

The initial step for the batch ethanol fermentation is the yeast inoculation, covering the hydration of the yeast. 66 lbs of the active dry yeasts of *Saccharomyces Cerevisiae* strains (BioFerm™ from North American Bioproducts Corporation, Lawrenceville, Ga.) was mixed with make-up water from plant operations to about 5% solid slurry. The slurry mixing is carried out in 360 gal Yeast Blending Tank at 100° F. for 20-30 minutes with good agitation. At an early stage of yeast hydration, 2 lbs of igneous phyllosilicate FIR-inducing natural minerals ultra-fine powder (about 1,200 mesh ACTIVA Bio-Mineral™ (II) from ACTIVA BioGreen, Inc., Wood Dale, Ill.) was added to Yeast Blending Tank after making a 20-25% solid slurry with make-up water.

The next step is the conditioning/propagating of the yeast under operating conditions favorable for rapid growth of the yeast. The jet-cooked and liquefied mash with 31-32% dry solid was pumped slowly to an 18,000 gal Propagation Tank at a rate of 11.6 gpm, along with make-up water at 14 gpm. Approximately one hour after starting to fill the Propagation Tank, the hydrated yeast slurry mixture was introduced to the Propagation Tank, along with 3 gal of a starch hydrolysis enzyme of glucoamylase (Sprizyme® fuel from Novozymes North America, Inc., Franklinton, N.C.). Further, 1 lb of antimicrobials (Lactoside™ from Ethanol Technology) was also added to the Propagation Tank after the completion of discharging the yeast slurry. In addition, 150 lbs of urea prill (47% N from Hydrite Chemical Co., Waterloo, Iowa) was added to the Propagation Tank to provide free-amino-nitrogen required for the yeast biosynthesis. The yeast incubation was continued so as to achieve a stable maximum yeast growth for about 8 hours under good agitation and until the tank was completely filled with low mash slurry of 12 Brix at 92-94° F. During the propagation process, compressed air was introduced through a sparger at the bottom of the tank in order to promote the growth of yeasts. Sulfuric acid (from Hydrite Chemical Co., Waterloo, Iowa) was used to adjust pH around 3.8-4.2 during the yeast conditioning process.

Prior to discharging the inoculated yeast slurry to the fermenter at the end of conditioning, a propagation sample was collected for the yeast cell count and HPLC analysis.

The next main step is the simultaneous saccharification and fermentation process to produce ethanol from fermentable sugars via an Embden-Meyerhof-Pamas (EMP) glycolysis pathway. The cooked and liquefied mash with 24 Brix including 48% backset was pumped at 1,150 gpm to a 730,000 gal fermenter. About 30 minutes after starting to fill the fermenter with the mash, discharge of the inoculated yeast slurry to the fermenter was started, for one and a half hours. At the beginning of filling the fermenter, 1,200 lbs urea prill (47% N from Hydrite Chemical Co., Waterloo, Iowa) was introduced to the fermenter and sulfuric acid was used to adjust the pH of the initial fermenting slurry to around 3.7-4.2. In addition, antimicrobials (Lactoside™ from Ethanol Technology) was added to the fermenter up to 1 lb. The temperature of the fermenter was set at 92° F. under good agitation.

During the fermentation cycle, an enzyme of glucoamylase (Sprizyme® fuel from Novozymes North America, Inc., Franklinton, N.C.) was employed for the hydrolysis of starch by sending the initial slug of 35 gal to the fermenter at the beginning and continuously feeding at a rate of 480 ml/min for additional 9 hours. During the saccharification/fermentation cycle, the total amount of glucoamylase fed to the fermenter was 107 gal that are equivalent to 0.45 amyloglucosidase units (AGU) per gram dry solid.

During the saccharification/fermentation cycle, several slurry samples were collected from the fermenter for the yeast cell count and HPLC analysis at 6, 10, 25, 39 and 45 hours intervals, along with the final drop sample.

The plant trial was continued for 11 days, including 15 fermentation batches. Using a color indicator of methylene blue and Hemacytometer's chambers, each fermentation sample was examined via a microscope at a 40 magnification (Nikon Model No. TE 2000 with a Motic digital camera) for the determination of CFU counts, viability index and budding index. The average yeast cell counts data during the plant trial are compiled in Table 2.

TABLE 2

Average Yeast Cell Count during SSF

| Sample | Budding Index (%) | Cell Density (million/ml) | Viability (%) |
|---|---|---|---|
| 10 hr SSF | 32.3 | 122.5 | 64.5 |
| 18 hr | 14.2 | 153.8 | 75.0 |
| 25 hr | 16.7 | 174.7 | 75.9 |
| 32 hr | 15.7 | 171.2 | 76.2 |
| 39 hr | 13.0 | 177.4 | 73.6 |
| 45 hr | 16.1 | 175.5 | 72.5 |

Using HPLC (Shimadzu Model No. LC28), the average HPLC analysis data during the plant trial are also compiled in Table 2A.

TABLE 2A

Sugars and Fermentation Products Distribution

HPLC Analysis Data (g/l based on dextrose equivalent)

| Sample | DP4+ | DP3 | Maltose | Glucose | Lactic | Glycerol | Acetic | Ethanol |
|---|---|---|---|---|---|---|---|---|
| Propagation | 51.72 | 1.78 | 12.74 | 39.89 | 0.88 | 9.69 | 2.81 | 84.52 |
| 10 hr SSF | 137.81 | 10.00 | 31.05 | 76.38 | 1.11 | 8.90 | 0.70 | 41.67 |
| 18 hr | 98.28 | 4.22 | 25.47 | 47.82 | 1.08 | 11.25 | 0.42 | 105.26 |
| 25 hr | 68.14 | 2.11 | 8.74 | 30.77 | 1.12 | 13.30 | 0.56 | 161.02 |
| 32 hr | 43.51 | 1.67 | 5.58 | 16.11 | 1.12 | 14.19 | 0.84 | 196.63 |
| 39 hr | 25.57 | 1.33 | 5.26 | 6.57 | 1.04 | 14.28 | 0.84 | 218.74 |
| 45 hr | 19.00 | 1.11 | 5.26 | 2.74 | 1.04 | 14.48 | 0.84 | 227.35 |
| 53 hr | 16.30 | 0.89 | 5.26 | 1.63 | 1.05 | 14.58 | 0.98 | 233.22 |

DP4+ dextrins are substituted with DP4 with a degree of polymerization of 4 for the estimation of dextrose equivalent data, unless specified otherwise.

Example 3

A third plant trial was conducted at an ethanol production plant for 7 days using igneous phyllosilicate FIR-inducing natural minerals. This modern plant uses a dry milling corn process incorporating the Simultaneous Saccharification and Fermentation (SSF) technology. The plant has a capacity of 48 million gallons of the fuel ethanol production per year using No. 2 yellow corn. The plant trial differs from the other examples described here in terms of a tight control of the saccharification rate during the fermentation cycle.

The initial step for the batch ethanol fermentation is the yeast inoculation, covering the hydration of the yeast. 100 lbs of the active dry yeasts of *Saccharomyces Cerevisiae* strains (Thermosacc® from Ethanol Technology, Milwaukee, Wis.) was mixed with make-up water from plant operations for about 5% solid slurry. The slurry mixing is carried out in 360 gal Yeast Blending Tank at 100° F. for 20-30 minutes with good agitation. The foregoing yeast hydration was repeated one hour after the initial hydration. At the $2^{nd}$ stage of yeast hydration, 4 lbs of igneous phyllosilicate FIR-inducing natural minerals ultra-fine powder (about 1,200 mesh ACTIVA Bio-Mineral™ (II) from ACTIVA BioGreen, Inc., Wood Dale, Ill.) was added to Yeast Blending Tank after making a 20-25% solid slurry with make-up water.

The next step is the conditioning/propagating of the yeast under operating conditions favorable for rapid growth of the yeast. The jet-cooked and liquefied mash with 32-33% dry solid was pumped slowly to an 18,000 gal Propagation Tank at a rate of 11 gpm, along with make-up water at 11 gpm. Approximately one hour after starting to fill the Propagation Tank, the initial hydrated yeast slurry mixture was introduced to the Propagation Tank. The $2^{nd}$ batch of the hydrated yeast slurry mixture was added to the fermenter after one hour. Further, 2 lbs of yeast foods (AYF 1177™ from Ethanol Technology, Milwaukee, Wis.) and 1 lb of antimicrobials (Lactoside™ from Ethanol Technology) was also added to the Propagation Tank after the completion of discharging the yeast slurry. In addition, 55 lbs of urea prill (47% N) was added to the Propagation Tank to provide free-amino-nitrogen required for the yeast biosynthesis. The yeast incubation was continued to achieve a stable maximum yeast growth for about 10 hours under good agitation until the tank was completely filled with low mash slurry of 12 Brix at 92-94° F. During the propagation process, compressed air was introduced through a sparger at the bottom of the tank in order to promote the growth of yeasts. Sulfuric acid was used to adjust the pH to around 5.0-5.4 during the yeast conditioning process.

Prior to discharging the inoculated yeast slurry to the fermenter at the end of conditioning, a propagation sample was collected for the yeast cell count and HPLC analysis.

The next main step is the simultaneous saccharification and fermentation process to produce ethanol from fermentable sugars via an Embden-Meyerhof-Pamas (EMP) glycolysis pathway. The cooked and liquefied mash with 24 Brix including 50% backset was pumped at 630 gpm to a 730,000 gal fermenter. About 30 minutes after starting to fill the fermenter with the mash, discharge of the inoculated yeast slurry to the fermenter was started, for one and a half hours. At the beginning of filling the fermenter, the urea solution with 2,500 lbs urea prill (47% N) was introduced to the fermenter, along with 25 lbs of zinc sulfate (22.5% Zn) and 280 lbs of magnesium sulfate (9.8% Mg). At the end of the fermenter filling, 8 lbs of the yeast foods (AYF1177 from Ethanol Technology) and 1 lb of antimicrobials (Lactoside from Ethanol Technology) was also added to the fermenter. Sulfuric acid was used to adjust the pH of the initial fermenting slurry to around 4.3-4.5. The temperature of the fermenter was set at 94° F. under good agitation but was cooled to 92° F. after the filling of the fermenter was completed. The temperature was controlled by recirculating the fermenting mash thru an external heat exchanging unit. Thereafter, the temperature was held steady for the rest of the saccharification/fermentation cycle.

During a fermentation cycle, an enzyme of glucoamylase (G-Zyme® 480 from Genencor International, Inc., Rochester, N.Y.) was employed for the hydrolysis of starch by starting to send the initial slug of 25 gal to the fermenter and thereafter an incremental feeding was employed at the rates of 340, 410 and 500 ml/min for 0-2. 2-4 and 4-14 hour intervals, respectively. At the end of 14 hour of continuous feeding, the final slug of 50 lbs glucoamylase was added to the fermenter. During the sacchrification/fermentation cycle, the total amount of glucoamylase fed to the fermenter was 190 gal that are equivalent to 0.39 glucoamylase units (GAU) per gram dry solid.

During the saccharification/fermentation cycle, several slurry samples were collected from the fermenter for the yeast cell count and HPLC analysis at 6, 12, 18, 24, 36 and 48 hours intervals, along with the final drop sample.

The plant trial was continued for 7 days, including 10 fermentation batches. The average yeast cell count data during the plant trial are compiled in Table 3.

TABLE 3

Average Yeast Cell Count during Propagation and SSF

| Sample | Budding Index (%) | Cell Density (million/ml) | Viability (%) |
|---|---|---|---|
| Propagation | 41.5 | 242.4 | 95.4 |
| 6 hr SSF | 30.5 | 87.0 | 76.1 |
| 12 hr | 27.8 | 159.8 | 90.4 |
| 18 hr | 29.1 | 142.0 | 91.7 |
| 24 hr | 29.2 | 159.4 | 91.7 |
| 36 hr | 23.3 | 172.0 | 89.5 |

The average HPLC analysis data during the plant trial are also compiled in Table 3A.

TABLE 3A

Sugars and Fermentation Products Distribution

| | HPLC Analysis Data (g/l based on dextrose equivalent) | | | | | | | |
|---|---|---|---|---|---|---|---|---|
| Sample | DP4+ | DP3 | Maltose | Glucose | Lactic | Glycerol | Acetic | Ethanol |
| Propagation | 73.87 | 13.68 | 18.32 | 4.64 | 0.37 | 4.65 | 0 | 52.89 |
| 6 hr SSF | 230.82 | 25.23 | 24.30 | 15.59 | 0.58 | 5.26 | 0.06 | 35.90 |
| 12 hr | 157.58 | 26.81 | 42.71 | 18.66 | 0.81 | 6.87 | 0 | 66.66 |
| 18 hr | 123.15 | 8.92 | 51.32 | 11.85 | 0.74 | 7.75 | 0 | 106.90 |
| 24 hr | 86.25 | 0 | 37.50 | 6.21 | 0.81 | 8.91 | 0 | 158.93 |
| 36 hr | 24.25 | 2.46 | 5.26 | 8.93 | 0.84 | 10.68 | 0.49 | 235.86 |
| 48 hr | 10.32 | 0.86 | 5.86 | 1.24 | 0.89 | 10.92 | 0.63 | 257.20 |

DP4+ dextrins are substituted with DP4 with a degree of polymerization of 4 for the estimation of dextrose equivalent data, unless specified otherwise.

Example 4

A fourth plant trial was conducted at an ethanol production plant for 11 days using igneous phyllosilicate FIR-inducing natural minerals. This modern plant uses a dry milling corn process incorporating the Simultaneous Saccharification and Fermentation (SSF) technology. The plant has a capacity of 45 million gallons of the fuel ethanol production per year using No. 2 yellow corn. This plant trial differs from the other examples described here mainly in terms of high level use of the yeast foods.

The initial step for the batch ethanol fermentation is the yeast inoculation, covering the hydration of the yeast. 44 lbs of the active dry yeasts of *Saccharomyces Cerevisiae* strains (Ethanol Red™ from LeSafre Yeast Corporation, Milwaukee, Wis., Product No. 42138) was mixed with make-up water from plant operations for about 5% solid slurry. The slurry mixing was carried out in a 360 gal Yeast Blending Tank at 100° F. for 20-30 minutes with good agitation. At an early stage of yeast hydration, 2 lbs of igneous phyllosilicate FIR-inducing natural minerals ultra-fine powder (about 1,200 mesh ACTIVA Bio-Mineral™ (II) from ACTIVA BioGreen, Inc., Wood Dale, Ill.) was added to Yeast Blending Tank after making a 20-25% solid slurry with make-up water.

The next step is the conditioning/propagating of the yeast under operating conditions favorable for rapid growth of the yeast. The jet-cooked and liquefied mash with 32-33% dry solid was pumped slowly to an 18,000 gal Propagation Tank at a rate of 18 gpm, along with make-up water at 16 gpm. Approximately 30 minutes after starting to fill the Propagation Tank, the hydrated yeast slurry mixture was introduced to the Propagation Tank, along with 2 gal of a starch hydrolyzing enzyme of glucoamylase (Sprizyme® from Novozymes North America, Inc., Franklinton, N.C.). Further, 50 lbs of yeast foods (AYF 1177™ from Ethanol Technology, Milwaukee, Wis.) and 1 lb of antimicrobials (Lactoside™ from Ethanol Technology) was also added to the Propagation Tank after the completion of discharging the yeast slurry. In addition, 200 lbs of urea prill (47% N) was added to Propagation Tank to provide free-amino-nitrogen required for the yeast biosynthesis. The yeast incubation was continued to achieve a stable maximum yeast growth for 7-8 hours under good agitation until the tank was completely filled with low mash slurry of 12 Brix at 90° F. During the propagation process, compressed air was introduced through a sparger at the bottom of the tank in order to promote the growth of yeasts. Sulfuric acid was used to adjust the pH to around 5.0-5.4 during the yeast conditioning process.

Prior to discharging the inoculated yeast slurry to the fermenter at the end of conditioning, a propagation sample was collected for the yeast cell count and HPLC analysis.

The next main step is the simultaneous saccharification and fermentation process to produce ethanol from fermentable sugars via an Embden-Meyerhof-Pamas (EMP) glycolysis pathway. The cooked and liquefied mash with 24 Brix including about 48% backset was pumped at 650 gpm to a 730,000 gal fermenter. About 10-15 minutes after starting to fill the fermenter with the mash, discharge of the inoculated yeast slurry to the fermenter was started, for one and a half hours. At beginning of filling the fermenter, the urea solution with 950 lbs urea prill was introduced to the fermenter and 96% concentrated sulfuric acid was used to adjust the pH of the initial fermenting slurry to around 4.6-4.8. Another type of antimicrobials (Allpen™ from Ethanol Technology) was added to the fermenter up to 3 lbs. When the fermenter was 50% filled, an additional 1,250 lbs urea (47% N) was added to the fermenter, along with 2 lbs of the antimicrobials (Allpen™). The temperature of the fermenter was set at 92° F. under good agitation but was cooled to 90° F. at the middle of a fermentation cycle via a external heat exchanging unit by recirculating the fermenting mash. The temperature was held steady for the second half of the fermentation cycle.

During a fermentation cycle, an enzyme of glucoamylase (Sprizyme® from Novozymes North America. Inc., Franklinton, N.C.) was employed for the hydrolysis of starch by sending the initial slug of 75 gal to the fermenter at the beginning, along with 8 gal protease. An additional 100 gal was added at 50% level of the fermenter. Thereafter continuously feeding glucoamylase at a rate of 210 ml/min for additional 16 hours. During the saccharification/fermentation cycle, the total amount of glucoamylase fed to the fermenter was 230 gal that are equivalent to 0.90 amyloglucosidase units (AGU) per gram dry solid.

During the saccharification/fermentation cycle, several slurry samples were collected from the fermenter for the yeast cell count and HPLC analysis at 10, 18, 25, 32, 39 and 45 hours intervals, along with the final drop sample.

The plant trial was continued for 11 days, including 13 fermentation batches. The measurement of yeast cell counts was conducted via a microscope using a color indicator of methylene blue and the average yeast cell count data during the plant trial are compiled in Table 4.

TABLE 4

Average Yeast Cell Count during Propagation and SSF

| Sample | Budding Index (%) | Cell Density (million/ml) | Viability (%) |
|---|---|---|---|
| Propagation | 32.9 | 178.4 | 92.1 |
| 10 hr SSF | 24.6 | 186.4 | 87.6 |
| 25 hr | 16.5 | 210.7 | 88.7 |

The average HPLC analysis data via Shimadzu Model No. LC-10AT during the plant trial are also compiled in Table 4A.

TABLE 4A

Sugars and Fermentation Products Distribution

| | HPLC Analysis Data (g/l based on dextrose equivalent) | | | | | | | |
|---|---|---|---|---|---|---|---|---|
| Sample | DP4+ | DP3 | Maltose | Glucose | Lactic | Glycerol | Acetic | Ethanol |
| Propagation | 56.40 | 8.94 | 29.59 | 27.70 | 0.25 | 3.99 | 0.18 | 28.51 |
| 10 hr SSF | 129.26 | 14.74 | 52.39 | 52.74 | 0.65 | 7.76 | 0.28 | 61.22 |
| 18 hr | 101.03 | 5.68 | 50.12 | 30.01 | 0.70 | 9.69 | 0.13 | 117.51 |
| 25 hr | 75.51 | 0.21 | 26.19 | 16.28 | 0.81 | 11.11 | 0.30 | 174.91 |
| 32 hr | 36.35 | 2.24 | 8.06 | 17.75 | 0.85 | 12.27 | 0.45 | 217.35 |
| 39 hr | 15.00 | 1.62 | 6.45 | 5.06 | 0.87 | 12.88 | 0.59 | 247.05 |
| 45 hr | 11.26 | 0.98 | 6.60 | 1.20 | 0.87 | 13.02 | 0.61 | 257.34 |

DP4+ dextrins are substituted with DP4 with a degree of polymerization of 4 for the estimation of dextrose equivalent data, unless specified otherwise.

COMPARATIVE EXAMPLES 1A TO 4A

Example 1A

The same fermentation batches were run for 9 days under identical operating conditions to Example 1, except omitting the addition of the FIR-inducing natural mineral powder to the fermenter. Throughout plant trials, extra efforts were made to maintain the same dry solid level as that of Example 1 for a fair comparison for the impact of the mineral addition on saccharification and fermentation performances.

The plant trial was continued to process 25 fermentation batches and the average yeast cell count data was measured to be 180-200 millions/ml.

Using HPLC (Waters Breeze Model 2410 with Refractive Index Detector from Waters Corp., Milford, Mass.), each fermentation sample was analyzed for a fermentation product distribution. Average ethanol productivity based on dextrose equivalent (DE) during the trial was derived to be 235.39 g/l with a standard deviation of 5.67.

Results and Discussion

Accordingly, an embodiment of the present invention with the employment of FIR-inducing minerals as illustrated in Example 1 yields a positive impact on the growth of yeast cells during a fermentation cycle, showing about 10-20% higher CFU's than those of Example 1A.

The average ethanol yield data are compared for demonstrating the improvement in one embodiment of the present invention over the reference data as listed in Table 5.

TABLE 5

Comparison of Ethanol Yield based on Dextrose Equivalent (DE)

| Fermentation Time | Ethanol Yield of Reference Batches (g/l) | Ethanol Yield of Example 1 (g/l) | Improvement over Reference (g/l) |
|---|---|---|---|
| 48 hr | 235.39 ± 5.67 | 244.47 ± 8.43 | 9.08 |

The results of Table 5 show a positive impact of the addition of FIR-inducing minerals on ethanol productivity, showing about 3.9% improvement over that of the reference batches.

Example 2A

The same fermentation batches were run under identical operating conditions to Example 2, except omitting the addition of the FIR-inducing natural mineral powder to the fermenter. Throughout plant trials, extra efforts were made to maintain the same dry solid level as that of Example 2 for a fair comparison for the impact of the mineral addition on saccharification and fermentation performances.

The plant reference runs were carried out for 16 days, including 20 fermentation batches. The average yeast cell count data during the plant reference runs are compiled in Table 6.

TABLE 6

Average Yeast Cell Count during SSF

| Sample | Budding Index (%) | Cell Density (million/ml) | Viability (%) |
|---|---|---|---|
| 10 hr SSF | 31.1 | 128.5 | 72.9 |
| 18 hr | 18.4 | 162.6 | 75.5 |
| 25 hr | 19.1 | 158.6 | 76.9 |
| 32 hr | 18.0 | 170.6 | 75.5 |
| 39 hr | 16.9 | 163.4 | 72.2 |
| 45 hr | 17.9 | 164.5 | 68.4 |

The average HPLC analysis data during the plant reference batches are also compiled in Table 6A.

TABLE 6A

Sugars and Fermentation Products Distribution

HPLC Analysis Data (g/l based on dextrose equivalent)

| Sample | DP4+ | DP3 | Maltose | Glucose | Lactic | Glycerol | Acetic | Ethanol |
|---|---|---|---|---|---|---|---|---|
| Propagation | 59.23 | 2.11 | 13.26 | 11.19 | 0.86 | 10.66 | 0.28 | 102.91 |
| 10 hr SSF | 140.51 | 10.22 | 30.63 | 68.04 | 1.11 | 8.90 | 0.56 | 43.44 |
| 18 hr | 127.72 | 7.22 | 23.47 | 41.60 | 1.06 | 10.76 | 0.42 | 93.52 |
| 25 hr | 75.30 | 2.22 | 10.74 | 29.28 | 1.09 | 13.01 | 0.56 | 154.76 |
| 32 hr | 51.72 | 1.78 | 5.90 | 13.00 | 1.02 | 13.79 | 0.70 | 192.91 |
| 39 hr | 34.48 | 1.33 | 5.05 | 5.07 | 1.00 | 14.09 | 0.70 | 212.67 |
| 45 hr | 24.98 | 1.11 | 4.84 | 1.72 | 1.00 | 14.28 | 0.70 | 223.63 |
| 53 hr | 19.59 | 0.89 | 4.74 | 1.23 | 1.00 | 14.28 | 0.84 | 228.33 |

Results and Discussion

The average viable yeast cell count data of colonial forming units (CFU) are compared to an embodiment of the present invention as in Example 2 as listed in Table 6B.

TABLE 6B

Comparison of Viable CFU

| Fermentation Time | CFU of Reference Batches (Table 6) (million/ml) | CFU of Example 2 (Table 2) (million/ml) | Improvement over Reference (%) |
|---|---|---|---|
| 10 hr | 93.7 | 79.0 | −15.7 |
| 18 hr | 122.8 | 115.3 | −6.1 |
| 25 hr | 122.0 | 132.5 | 8.6 |
| 32 hr | 128.8 | 130.5 | 1.3 |

TABLE 6B-continued

Comparison of Viable CFU

| Fermentation Time | CFU of Reference Batches (Table 6) (million/ml) | CFU of Example 2 (Table 2) (million/ml) | Improvement over Reference (%) |
|---|---|---|---|
| 39 hr | 118.0 | 130.6 | 10.7 |
| 45 hr | 112.5 | 127.2 | 13.1 |

Figure 5:
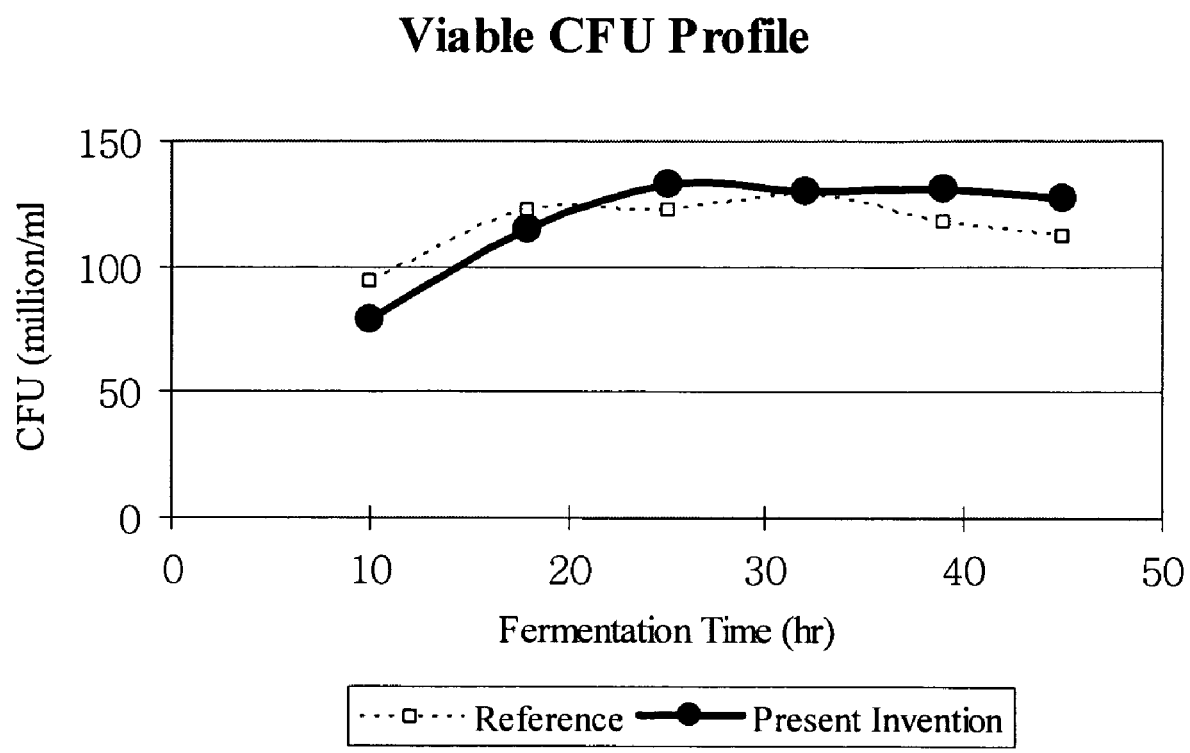
FIGS. 5, 6 and 7 show the results of examples of the embodiments, comparing a viable colonial forming unit (CFU) profile of the embodiments of the present invention to that of the reference batches conducted at industrial ethanol plants with the Simultaneous Saccharification and Fermentation (SSF) process.

The final CFU data in Table 6B show the average viable cell count was increased up to 13% in the presence of FIR-inducing minerals, compared to those of the average data of the reference batches. FIG. 5 exhibits the comparison of viable CFU data as a function of fermentation time, showing a positive impact of FIR-inducing natural minerals on the growth of yeast cells.

The average ethanol yield data are compared for demonstrating the improvement in one embodiment of the present invention over the reference data as listed in Table 6C.

TABLE 6C

Comparison of Ethanol Yield based on Dextrose Equivalent (DE)

| Fermentation Time | Ethanol Yield of Reference Batches (Table 6A) (g/l) | Ethanol Yield of Example 2 (Table 2A) (g/l) | Improvement over Reference (g/l) |
|---|---|---|---|
| 10 hr | 43.44 | 41.67 | −1.77 |
| 18 hr | 93.52 | 105.26 | 11.74 |
| 25 hr | 154.76 | 161.02 | 6.26 |
| 32 hr | 192.91 | 196.63 | 3.72 |
| 39 hr | 212.67 | 218.74 | 6.07 |
| 45 hr | 223.63 | 227.35 | 3.72 |
| 53 hr | 228.33 | 233.22 | 4.89 |

The results of Table 6C show a positive impact of the addition of FIR-inducing minerals on ethanol productivity, showing about 2.1% improvement over that of the reference batches.

In addition, the total saccharification productivities excluding DP4+ on the basis of HPLC data during a fermentation cycle are also compared as listed in Table 6D.

TABLE 6D

Comparison of Total Saccharification based on Dextrose Equivalent (DE)

| Fermentation Time | Total Saccharification of Reference Batches (Table 6A) (g/l) | Total Saccharification of Example 2 (Table 2A) (g/l) | Improvement over Reference (g/l) |
|---|---|---|---|
| 10 hr | 162.85 | 169.83 | 6.98 |
| 18 hr | 178.10 | 195.53 | 17.43 |
| 25 hr | 211.69 | 217.44 | 5.75 |
| 32 hr | 229.08 | 236.11 | 7.03 |
| 39 hr | 239.95 | 248.06 | 8.11 |
| 45 hr | 247.27 | 252.74 | 5.47 |
| 53 hr | 251.28 | 257.63 | 6.35 |

The results in Table 6D indicate that the addition of FIR-inducing minerals was found to enhance the final average saccharification productivity by 2.5% over that of the reference batches.

Example 3A

The same fermentation batches were run under identical operating conditions to Example 3, except omitting the addition of the FIR-inducing natural mineral powder to the fermenter. Throughout plant trials, extra efforts were made to maintain the same dry solid level as that of Example 3 for a fair comparison for the impact of the mineral addition on saccharification and fermentation performances.

The plant reference runs were carried out for 15 days, including 17 fermentation batches. The average yeast cell count data during the plant reference runs are compiled in Table 7.

TABLE 7

Average Yeast Cell Count during Propagation and SSF

| Sample | Budding Index (%) | Cell Density (million/ml) | Viability (%) |
|---|---|---|---|
| Propagation | 37.2 | 224.1 | 94.3 |
| 6 hr SSF | 27.3 | 68.6 | 82.2 |
| 12 hr | 26.9 | 120.3 | 90.8 |
| 18 hr | 23.3 | 105.9 | 90.6 |
| 24 hr | 24.6 | 121.2 | 89.1 |
| 36 hr | 23.3 | 118.9 | 87.3 |

The average HPLC analysis data during the plant reference batches are also compiled in Table 7A.

TABLE 7A

Sugars and Fermentation Products Distribution

| | HPLC Analysis Data (g/l based on dextrose equivalent) | | | | | | | |
|---|---|---|---|---|---|---|---|---|
| Sample | DP4+ | DP3 | Maltose | Glucose | Lactic | Glycerol | Acetic | Ethanol |
| Propagation | 62.42 | 10.54 | 24.08 | 7.35 | 0.31 | 4.21 | 0 | 55.04 |
| 6 hr SSF | 237.37 | 27.17 | 27.12 | 18.96 | 0.54 | 4.43 | 0.13 | 26.12 |
| 12 hr | 172.03 | 28.03 | 42.44 | 18.16 | 0.73 | 5.96 | 0.04 | 62.34 |
| 18 hr | 121.68 | 10.44 | 50.01 | 15.32 | 0.69 | 6.77 | 0 | 99.84 |
| 24 hr | 86.15 | 0.13 | 41.10 | 12.63 | 0.71 | 7.79 | 0 | 157.05 |
| 36 hr | 29.45 | 2.54 | 5.33 | 14.72 | 0.80 | 9.06 | 0.25 | 226.72 |
| 48 hr | 10.76 | 0.93 | 5.17 | 3.47 | 0.75 | 9.39 | 0.59 | 253.19 |

Results and Discussion

The viable yeast cell count data of colonial forming units (CFU) are compared to an embodiment of the present invention as in Example 3, after deriving the yeast cell growth ratio on the basis of each CFU data from prior propagations as listed in Table 7B.

TABLE 7B

Comparison of Growth Ratio of Viable Yeast Cells

| | Reference Batches (Table 7) | | | Samples of Example 3 (Table 3) | | | |
| --- | --- | --- | --- | --- | --- | --- | --- |
| Fermentation Time (hr) | Viable CFU (x) (million/ml) | Initial CFU ($x_o$) (million/ml) | Growth Ratio ($x/x_o$) | Viable CFU (x) (million/ml) | Initial CFU ($x_o$) (million/ml) | Growth Ratio ($x/x_o$) | Improvement over Reference (%) |
| 6 hr | 56.4 | 12.19 | 4.6 | 66.2 | 13.36 | 5.0 | 8.7 |
| 12 hr | 109.2 | 6.09 | 17.9 | 144.4 | 6.68 | 21.6 | 20.7 |
| 18 hr | 95.9 | 4.34 | 22.1 | 130.2 | 5.22 | 24.9 | 12.7 |
| 24 hr | 108.0 | 4.34 | 24.9 | 146.2 | 5.22 | 28.0 | 12.4 |
| 36 hr | 103.8 | 4.34 | 23.9 | 153.9 | 5.22 | 29.5 | 23.4 |

Figure 6:
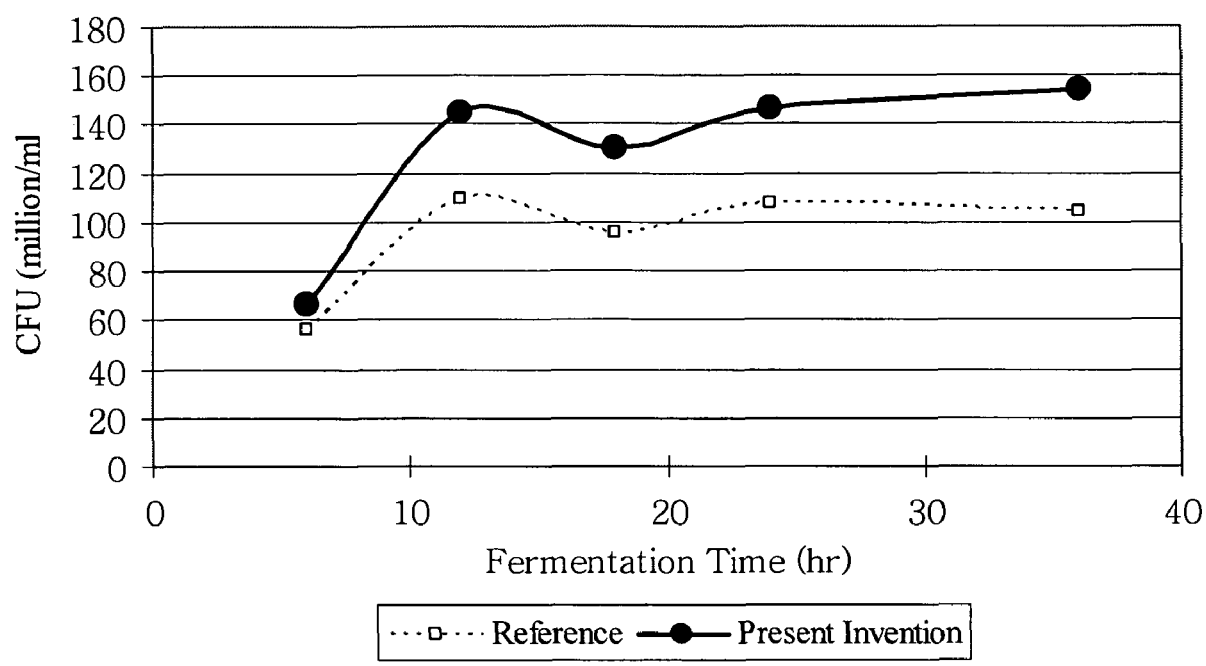

The final CFU data in Table 7B show the average viable cell count was increased by 17-48% in the presence of FIR-inducing minerals, compared to those of the average data of the reference batches. The yeast growth factor was also estimated to be increased by 9-23% in the presence of FIR-inducing minerals, as tabulated in Table 7B. FIG. 6 exhibits the comparison of viable CFU data as a function of fermentation time, showing a positive impact of FIR-inducing natural minerals on the growth of yeast cells.

During the yeast propagation, the average CFU in the presence of FIR-inducing minerals was also increased by 12.4% as tabulated in Tables 3 and 7.

The average ethanol yield data are compared for demonstrating the improvement in one embodiment of the present invention over the reference data as listed in Table 7C.

TABLE 7C

Comparison of Ethanol Yield based on Dextrose Equivalent (DE)

| Fermentation Time | Ethanol Yield of Reference Batches (Table 7A) (g/l) | Ethanol Yield of Example 3 (Table 3A) (g/l) | Improvement over Reference (g/l) |
| --- | --- | --- | --- |
| 6 hr | 26.12 | 35.90 | 9.78 |
| 12 hr | 62.34 | 66.66 | 4.32 |
| 18 hr | 99.84 | 106.90 | 7.06 |
| 24 hr | 157.05 | 158.93 | 1.88 |
| 36 hr | 226.72 | 235.86 | 9.14 |
| 48 hr | 253.19 | 257.20 | 4.01 |

The results of Table 7C show a positive impact of the addition of FIR-inducing minerals on ethanol productivity, showing about 1.6% improvement over that of the reference batches.

In addition, the total saccharification productivities during a fermentation cycle are also compared as listed in Table 7D.

TABLE 7D

Comparison of Total Saccharification based on Dextrose Equivalent (DE)

| Fermentation Time | Total Saccharification of Reference Batches (Table 7A) (g/l) | Total Saccharification of Example 3 (Table 3A) (g/l) | Improvement over Reference (g/l) |
| --- | --- | --- | --- |
| 6 hr | 104.46 | 106.93 | 2.47 |
| 12 hr | 157.70 | 162.51 | 4.81 |
| 18 hr | 183.08 | 187.48 | 4.40 |
| 24 hr | 219.41 | 212.36 | −7.05 |
| 36 hr | 259.42 | 264.52 | 5.10 |
| 48 hr | 273.50 | 277.60 | 4.10 |

The results in Table 7D indicate that the addition of FIR-inducing minerals was found to enhance the final average saccharification productivity excluding DP4+ on the basis of HPLC data by 1.5% over that of the reference batches.

Example 4A

The same fermentation batches were run under identical operating conditions to Example 4, except omitting the addition of the FIR-inducing natural mineral powder to the fermenter. Throughout plant trials, extra efforts were made to maintain the same dry solid level as that of Example 3 for a fair comparison for the impact of the mineral addition on saccharification and fermentation performances.

The plant reference runs were carried out for 6 days, including 8 fermentation batches. The average yeast cell count data during the plant reference runs are compiled in Table 8.

TABLE 8

Average Yeast Cell Count during Propagation and SSF

| Sample | Budding Index (%) | Cell Density (million/ml) | Viability (%) |
|---|---|---|---|
| Propagation | 33.3 | 153.5 | 87.6 |
| 10 hr SSF | 28.0 | 144.3 | 83.5 |
| 25 hr | 16.3 | 161.8 | 86.8 |

The average HPLC analysis data during the plant reference batches are also compiled in Table 8A.

TABLE 8A

Sugars and Fermentation Products Distribution

HPLC Analysis Data (g/l based on dextrose equivalent)

| Sample | DP4+ | DP3 | Maltose | Glucose | Lactic | Glycerol | Acetic | Ethanol |
|---|---|---|---|---|---|---|---|---|
| Propagation | 51.62 | 6.54 | 29.70 | 35.47 | 0.71 | 3.22 | 0.23 | 20.43 |
| 10 hr SSF | 82.89 | 3.57 | 39.25 | 101.34 | 0.79 | 7.08 | 1.14 | 51.05 |
| 18 hr | 72.22 | 3.50 | 27.93 | 66.48 | 0.85 | 9.90 | 0.65 | 117.82 |
| 25 hr | 43.13 | 2.40 | 10.20 | 51.18 | 0.80 | 11.28 | 0.56 | 168.79 |
| 32 hr | 17.09 | 1.94 | 6.93 | 33.37 | 0.77 | 12.27 | 0.63 | 212.42 |
| 39 hr | 11.62 | 1.02 | 6.80 | 3.64 | 0.77 | 12.87 | 0.68 | 242.80 |
| 45 hr | 10.64 | 0.77 | 6.88 | 2.10 | 0.76 | 12.62 | 0.73 | 246.87 |

Results and Discussion

The viable yeast cell count data of colonial forming units (CFU) are compared to an embodiment of the present invention as in Example 4 as listed in Table 8B.

TABLE 8B

Comparison of Viable CFU

| Fermentation Time | CFU of Reference Batches (Table 8) (million/ml) | CFU of Example 4 (Table 4) (million/ml) | Improvement over Reference (%) |
|---|---|---|---|
| Propagation | 134.4 | 164.3 | 22.2 |
| 10 hr | 120.5 | 163.3 | 35.5 |
| 25 hr | 140.4 | 186.9 | 33.1 |

Figure 7:
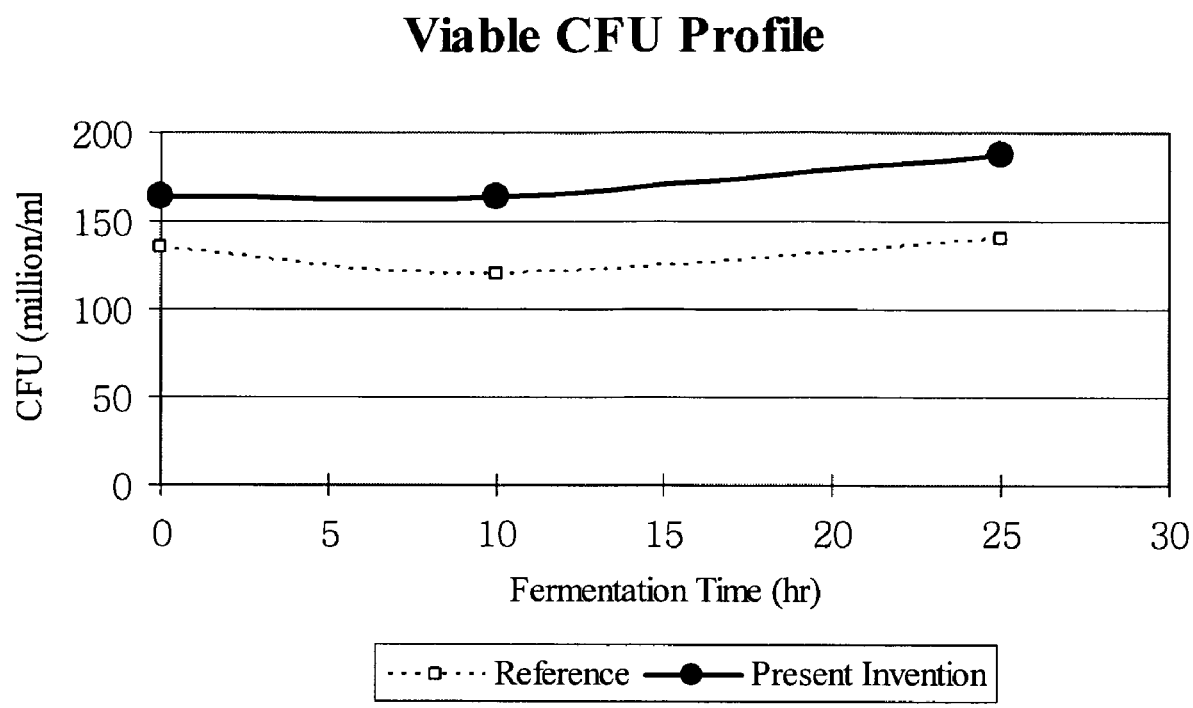

The final CFU data in Table 8B show the average viable cell count was increased up to 35% in the presence of FIR-inducing minerals, compared to those of the average data of the reference batches. FIG. 7 exhibits the comparison of viable CFU data as a function of fermentation time, showing a positive impact of FIR-inducing natural minerals on the growth of yeast cells.

During the yeast propagation, the average CFU in the presence of FIR-inducing minerals was also increased by 16.2% as tabulated in Tables 4 and 8.

The average ethanol yield data are compared for demonstrating the improvement in one embodiment of the present invention over the reference data as listed in Table 8C.

TABLE 8C

Comparison of Ethanol Yield based on Dextrose Equivalent (DE)

| Fermentation Time | Ethanol Yield of Reference Batches (Table 8A) (g/l) | Ethanol Yield of Example 4 (Table 4A) (g/l) | Improvement over Reference (g/l) |
|---|---|---|---|
| 10 hr | 51.05 | 61.22 | 10.17 |
| 18 hr | 117.82 | 117.51 | −0.31 |
| 25 hr | 168.79 | 174.91 | 6.12 |
| 32 hr | 212.42 | 217.35 | 4.93 |
| 39 hr | 242.80 | 247.05 | 4.25 |
| 45 hr | 246.87 | 257.34 | 10.47 |

The results of Table 8C show a positive impact of the addition of FIR-inducing minerals on ethanol productivity, showing about 4.2% improvement over that of the reference batches.

In addition, the total saccharification productivities during a fermentation cycle are also compared as listed in Table 8D.

TABLE 8D

Comparison of Total Saccharification based on Dextrose Equivalent (DE)

| Fermentation Time | Total Saccharification of Reference Batches (Table 8A) (g/l) | Total Saccharification of Example 4 (Table 4A) (g/l) | Improvement over Reference (g/l) |
|---|---|---|---|
| 10 hr | 204.22 | 189.78 | −14.44 |
| 18 hr | 227.12 | 213.82 | −13.30 |
| 25 hr | 245.21 | 229.81 | −15.40 |
| 32 hr | 268.33 | 258.98 | −9.35 |
| 39 hr | 268.59 | 274.53 | 5.94 |
| 45 hr | 270.74 | 280.61 | 9.87 |

The results in Table 8D indicate that the addition of FIR-inducing minerals was found to enhance the final average saccharification productivity excluding DP4+ on the basis of HPLC data by 3.6% over that of the reference batches.

As demonstrated in the foregoing examples, the addition of FIR-inducing minerals had a positive impact on the growth of microbes for the ethanol fermentation as well as the saccharification for the production of fermentable sugars.

The present invention has been described in Examples 1-4, and it is to be understood that the technology employed is intended for a typical exemplified description, that is, the scope of the invention is not intended to be limited by the illustrated examples and preferred embodiments.

Further, a variety of modifications and variations of the present invention are possible in light of the foregoing examples. Therefore, it is also to be understood that within the scope of the appended claims, the invention may be practiced otherwise than as explicitly described.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

What is claimed is:

1. A method for increasing the growth of mesophilic ethanologenic microbes, applying FIR-inducing natural minerals, which comprise at least one mineral selected from the group consisting of: agalmatolite, albite, anorthite, antigorite, aplite, betalite, biotite, char coal, chlorite, clinochlore, clinoptillolite, garnet, glauconite, illite, jade, kyanite, leonardite, mica, microcline, muscovite, olivine, orthoclase, pascalite, phlogopite, plagioclase, pyrophyllite, sanidine, sericite, sepiolite, serpentine, sillimanite, staurolite, tourmaline and volcano ash; to a fermenter filled with a fermentation mash under acidic conditions for a biomass conversion process, wherein the said microbes are exposed to a saccharide source, wherein the said microbes are yeast.

2. The method of claim 1, wherein the FIR emittance of FIR-inducing natural minerals is higher than about 0.90 on the basis of an ideal black body with wavelengths of 5 to 20 µm.

3. The method of claim 1, wherein the FIR-inducing natural minerals are a fine powder having particle sizes of at least about 400 mesh.

4. The method of claim 1, wherein the biomass conversion process is a biomass to ethanol process.

5. The method of claim 4, wherein the biomass to ethanol process comprises a batch process of saccharification, fermentation or simultaneous saccharification and fermentation.

6. The method of claim 4, wherein the biomass to ethanol process comprises a continuous saccharification and fermentation process.

7. The method of claim 1, in which the biomass for the biomass conversion process is selected from the group consisting of corn, barley, sorghum (milo), wheat, rye, rice, other cereal grains, cellulose, hemicellulose, lignocellulose, pectin, potatoes, and combinations thereof.

8. The method claim 1, in which the biomass for the biomass conversion process comprises corn.

9. The method of claim 1, in which the biomass for the biomass conversion process comprises fermentable carbon compound sources, inorganic nitrogen, phosphate and dissolved oxygen.

10. The method of claim 5, wherein the FIR-inducing natural minerals are introduced to a yeast propagation tank and a fermenter.

11. The method of claim 1, wherein the biomass conversion process is a biomass to yeast process.

12. The method of claim 11, wherein the yeast is selected from the group consisting of compressed bakery yeast, active dry yeast, creamy yeast, feed yeast, and yeast cultures.

13. The method of claim 11, wherein the FIR-inducing natural minerals are introduced to a culture fermenter, a seed propagator, or a fermenter.

14. The method of claim 1, wherein the amount of the FIR-inducing natural minerals is in the range of from 0.5 to 25% by weight based on the total initial weight of the microbes.

15. The method of claim 4, wherein the amount of the FIR-inducing natural minerals is in the range of from 0.5 to 25% by weight based on the total initial weight of the microbes.

16. The method of claim 11, wherein the amount of the FIR-inducing natural minerals is in the range of from 0.5- to 25% by weight based on the total initial weight of the microbes.

17. The method of claim 1, wherein the biomass conversion process comprises using a fermenter equipped with at least one device that emits FIR rays and/or a propagator equipped with at least one device that emits FIR rays.

18. The method of claim 11, wherein the biomass conversion process comprises using a fermenter equipped with at least one device that emits FIR rays and/or a propagator equipped with at least one device that emits FIR rays.

* * * * *